(12) United States Patent
Wang et al.

(10) Patent No.: US 10,981,873 B2
(45) Date of Patent: *Apr. 20, 2021

(54) NICOTINIC ACID OR ISONICOTINIC ACID COMPOUND AND USE THEREOF

(71) Applicant: ACADEMY OF MILITARY MEDICAL SCIENCES, Beijing (CN)

(72) Inventors: Hui Wang, Beijing (CN); Tao Li, Beijing (CN); Zhenyuan Miao, Beijing (CN); Jianxin Wang, Beijing (CN); Deyan Luo, Beijing (CN); Jie Huang, Beijing (CN); Chunlin Zhuang, Beijing (CN); Yuelin Wu, Beijing (CN)

(73) Assignee: ACADEMY OF MILITARY MEDICAL SCIENCES, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/317,114

(22) PCT Filed: Sep. 8, 2017

(86) PCT No.: PCT/CN2017/100984
§ 371 (c)(1),
(2) Date: Jan. 11, 2019

(87) PCT Pub. No.: WO2018/010702
PCT Pub. Date: Jan. 18, 2018

(65) Prior Publication Data
US 2019/0241522 A1   Aug. 8, 2019

(30) Foreign Application Priority Data

Jul. 12, 2016 (CN) .......................... 201610546453.3

(51) Int. Cl.
| | | |
|---|---|---|
| *C07D 213/79* | (2006.01) | |
| *C07D 213/80* | (2006.01) | |
| *C07D 213/803* | (2006.01) | |
| *A61P 31/04* | (2006.01) | |
| *A61K 31/455* | (2006.01) | |
| *A61K 31/44* | (2006.01) | |

(52) U.S. Cl.
CPC .......... *C07D 213/803* (2013.01); *A61K 31/44* (2013.01); *A61K 31/455* (2013.01); *A61P 31/04* (2018.01); *C07D 213/79* (2013.01); *C07D 213/80* (2013.01)

(58) Field of Classification Search
CPC ............................ C07D 213/79; C07D 213/80
USPC ........................................ 546/290; 514/350
See application file for complete search history.

(56) References Cited

U.S. PATENT DOCUMENTS 10,035,771 B2 * 7/2018 Wang .................. C07D 213/80

FOREIGN PATENT DOCUMENTS

| CN | 101704780 A | 5/2010 |
|---|---|---|
| CN | 103265478 A | 8/2013 |
| CN | 106243026 A | 12/2016 |
| WO | 2011/022721 A1 | 2/2011 |
| WO | 2014/187291 A1 | 11/2014 |

OTHER PUBLICATIONS

Banker et al., Prodrugs, Modern Pharmaceutics, 3rd edition, Revised and Expanded, pp. 451 and 596.*
Jordan "Tamoxifen " Nature Rev. v.2, p. 205-213 (2003).*
Ettmayer et al. "Lessons Learned from Marketed and Investigational Prodrugs." J. Med. Chem., (2004), 47(10): 2393-2404.*
Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2097-2106.*
Balant ed in Wolff et al. Burger's Medicinal Chemistry and Drug Discovery. 5th ed. vol. 1: Principles and Practice. pp. 949-982, 1996.*
Bundgaard, Design of Prodrugs, Chapter 1, p. 1, 1985.*
Silverman, Prodrugs and Drug Delivery Systems, The Organic Chemistry of Drug Design and Drug action, Chapter 8, pp. 352-400, 1992.*
Patani et al., "Bioisosterism, etc.," Chem. Rev. 96, 3147-3176. (Year: 1996).*
Arimitsu H. et al., "Purification of Fully Activated Clostridium Botulinum Serotype B Toxin for Treatment of Patients With Dystonia", Infection and Immunity 71(3):1599-1603 (Mar. 2003).
Black R.E. et al., "Hypersensitivity Reactions Associated With Botulinal Antitoxin", The American Journal of Medicine 69:567-570 (Oct. 1980).
Eubanks L.M. et al., "Identification of a Natural Product Antagonist Against the Botulinum Neurotoxin Light Chain Protease", ACS Med. Chem. Lett. 1:268-272 (2010).

(Continued)

*Primary Examiner* — Patricia L Morris
(74) *Attorney, Agent, or Firm* — Scully, Scott, Murphy & Presser, P.C.

(57) ABSTRACT

Disclosed are a nicotinic acid or isonicotinic acid compound and a use thereof. The compound is the compound shown in Formula I, or a pharmaceutically acceptable salt, ester or solvate thereof. Efficacy tests demonstrate that the nicotinic acid compound can inhibit *botulinum* toxin endopeptidase activity in vitro, and has a significant protective effect on mice poisoned with *botulinum* toxin. On this basis, the compound may be used to prepare a drug preventing and/or treating *botulinum* toxin exposure and/or poisoning.

Formula I

4 Claims, No Drawings

(56) References Cited

OTHER PUBLICATIONS

Gilsdorf J. et al., "Expression, Purification, and Characterization of Clostridium Botulinum Type B Light Chain", Protein Expression and Purification 46:256-267 (2006).
Hatheway C.H. et al., "Antitoxin Levels in Botulsim Patients With Trivalent Equine Botulism Antitoxin to Toxin Types A, B, and E", The Journal of Infectious Diseases 150(3):407-412 (Sep. 1984).
Li L. et al., "High-Level Expression, Purification, and Characterization of Recombinant Type A Botulinum Neurotoxin Light Chain", Protein Expression and Purification 17:339-344 (1999).
Malizio C.J. et al., "Purification of Clostridium Botulinum Type A Neurotoxin", Methods in Molecular Biology 145:27-39 (2000).
Pang Y-P et al., "Potent New Small-Molecule Inhibitor of Botulinum Neurotoxin Serotype A Endopeptidase Developed by Synthesis-Based Computer-Aided Molecular Design", PLoS One 4(11):e7730 (Nov. 2009).
Roxas-Duncan V. et al, "Identification and Biochemical Characterization of Small-Molecule Inhibitors of Clostridium Botulinum Neurotoxin Serotype A§", Antimicrobial Agents and Chemotherapy 53(8):3478-3486 (Aug. 2009).
Ruge D.R. et al., "Detection of Six Serotypes of Botulinum Neurotoxin Using Fluorogenic Reporters", Analytical Biochemistry 411:200-209 (2011).
International Search Report dated Nov. 29, 2017 received in International Application No. PCT/CN2017/100984, together with an English-language translation.
Anisimov, A.V., et al., "Synthesis of Sulfonyl and Sulfenyl Derivatives of Pyridine and 1,2,4-Triazole", Russian Journal of Organic Chemistry, 2006, pp. 918-921, vol. 42, No. 6.

\* cited by examiner

NICOTINIC ACID OR ISONICOTINIC ACID COMPOUND AND USE THEREOF

TECHNICAL FIELD

The present disclosure belongs to the medical field, and relates to a nicotinic acid- or isonicotinic acid-based compound and use thereof.

BACKGROUND ART

Toxins of *Clostridium* species comprise *botulinum* neurotoxins and tetanus toxins. The tetanus toxins are produced by *Clostridium tetani* under an anaerobic environment and can clinically cause tetanus. *Clostridium botulinum* neurotoxins (referred to as *botulinum* toxins for short) is a group of known proteins (including types A-G) which have strongest toxicity and are mainly produced by *Clostridium botulinum* under an anaerobic environment, with a median lethal dose of about 1 ng/kg for intravenous injection and a median lethal dose of about 3 ng/kg for inhalation. Common poisoning by *botulinum* toxins is mainly caused by consumption of contaminated food, introduction of toxins produced by infected wound into the body, and production of active toxins from toxin precursors through digestion in baby's intestinal tract. In addition, *botulinum* toxin type A has been widely used in the clinical treatment of dysfunction of cholinergic nerves and muscles, as well as in cosmetic wrinkle removal, which may cause the occurrence of systemic botulism symptoms due to overdose, misuse, and/or adverse reactions during the treatment. The incubation period of botulism is short, the course of disease is developing rapidly, the condition is serious, and the mortality rate is high. Human botulism is mainly caused by types A, B, E, and F, while type A has the strongest neurotoxicity to humans. The drugs currently used for prevention and treatment of botulism and tetanus are (type) specific anti-toxin horse serum, which can be effective for more than 80% of poisoned patients. However, these drugs have evident side effects, and it is reported clinically that serum sickness and allergic reactions occur in about 9% of clinical cases (Black R E, et al. *Am J Med,* 1980, 69: 567-570), which severely limits the use of horse serum antitoxins. There is an urgent need to find novel drugs which are safer and more effective.

Tetanus and botulism have a similar pathogenic process, in which C-terminus of the heavy chain of the toxin binds to ganglioside on the membrane of nerve cells, and the structure of the toxin is rearranged under the acidic environment to promote entrance of N-terminus of the heavy chain into the membrane and the unfolding of the light chain which, after the disulfide bond is reduced, is introduced into the cell as a zinc ion metalloenzyme to catalyze the cleavage of a class of intracellular substrate proteins (*botulinum* neurotoxins types A and E act on the synaptosome-associated protein SNAP-25, *botulinum* neurotoxins types B, D, F, G and tetanus toxin act on synaptic vesicle-associated membrane protein VAMP), thereby affecting the transfer of acetylcholine, interfering with the transmission of nerve impulses, and thus causing paralysis or excitation of motor nerves. If one or more of the 3 aspects including binding, introduction and catalysis are inhibited or hindered, the neurotoxicity of the toxin can be effectively inhibited. The design and development of catalytic inhibitors targeting the light chain of the toxin that has an enzymatic activity have become a research hotspot in recent years. Harry B et al. found 30 non-subtype inhibitors by in vitro high-throughput screening of natural extracts of plants, marine tissues, and fungi that can inhibit the toxins of *Clostridium* species, of which 5 extracts can inhibit both *Botulinum* toxins types B and E. Smith L A et al. found in 2009 that quinolinol derivative CB7969312 is a potential inhibitor that effectively neutralizes the toxicity of *botulinum* toxin type A to N2a cells by binding to the Zn catalytic region in the large hydrophobic pocket of the active site in light chain of the *botulinum* toxin type A (Roxas-Duncan, V, et al. *Agents Chemother.* 2009, 53:3478-3486; Pang, Y.-P. et al. *PLos One* 2009, 4, e7730). Janda K D et al. found in 2010 that lomofungin is able to inhibit the light chain of the *botulinum* toxin type A (Ki value of 6.7±0.7 uM), showing a typical non-competitive kinetics (Eubanks, L. M., et al. *ACS Med. Chem. Lett.* 2010, 1:268-272). These natural products or compounds reported have an inhibitory effect on the light chain of the toxin in vitro, and some natural products or compounds also have an inhibitory effect at the level of overall toxins and animal models, but there is still possibility for improvement in activity. In addition, most of the compounds reported so far have a type-specific toxin-inhibiting activity, and the cross-inhibition effect needs to be improved. Therefore, it is necessary to study and develop novel natural products or active compounds, which can have a wider range of in vitro inhibition and antagonism against *Clostridium* neurotoxins (multiple types of *botulinum* toxin and tetanus toxin), and can show a high anti-toxic activity at the level of overall animals, and from which to develop new therapeutic drugs.

SUMMARY

The object of the present disclosure is to provide a nicotinic acid- or isonicotinic acid-based compound and use thereof.

The present disclosure provides a novel nicotinic acid- or isonicotinic acid-based compound, comprising an acceptable salt, ester, solvate thereof, and the structural formula of the compound is of Formula I:

Formula I in the Formula I, $R_1$ and $R_2$ independently represent any one of the groups selecting from the group consisting of hydrogen and $-(CH_2)_m COOH$;

$R_3$, $R_4$, $R_5$, $R_6$ and $R_7$ independently represent any one of the groups selecting from the group consisting of hydrogen, hydroxyl, amino, halogen, lower alkyl, lower alkoxy, and lower cycloalkyl;

the lower alkyl refers to a linear or branched saturated aliphatic group having 1 to 6 carbon atoms;

the lower alkoxy refers to a linear or branched alkoxy group having 1 to 6 carbon atoms;

the lower cycloalkyl refers to a ring group having 3 to 7 carbon atoms;

X independently represents any one of the groups selecting from the group consisting of O, $-S=O$, and $-SO_2$;

m is 0, or 1, or 2, or 3.

Herein, said lower alkyl may specifically be methyl, ethyl, propyl, isopropyl, butyl, or t-butyl;

said lower alkoxy may specifically be methoxy, or ethoxy;

said lower cycloalkyl may specifically be cyclopropyl, cyclobutyl, cyclopentyl, cyclohexyl, or cycloheptyl;

said halogen may specifically be chloro, bromo, iodo or fluoro;

the pharmaceutically acceptable salt of the compound as shown in Formula I above is a kind of salts formed by a carboxy group substituted on the pyridine ring with a metal ion, or formed by a nitrogen atom in the pyridine ring with an organic or inorganic acid.

More preferably, the compound as shown in Formula I is selected from the group consisting of:

2-((2-((5-chloro-2-methoxyphenyl)amino)-2-oxoethyl) sulfonyl)isonicotinic acid, with the structural formula as shown in 2a;

2-((2-((5-chloro-2-phenoxyphenyl)amino)-2-oxoethyl) sulfonyl)nicotinic acid, with the structural formula as shown in 2b;

2-((2-((5-chloro-2-methoxyphenyl)amino)-2-oxoethyl) sulfinyl)nicotinic acid, with the structural formula as shown in 2c;

2-(2-((5-chloro-2-methoxyphenyl)amino)-2-oxoethoxy) nicotinic acid, with the structural formula as shown in 6a;

2-(2-((5-chloro-2-methoxyphenyl)amino)-2-oxoethoxy) isonicotinic acid, with the structural formula as shown in 6b.

2a
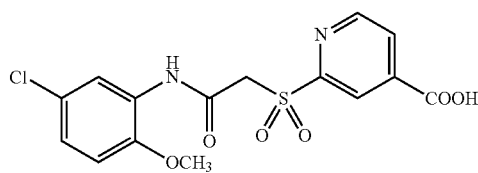

2b
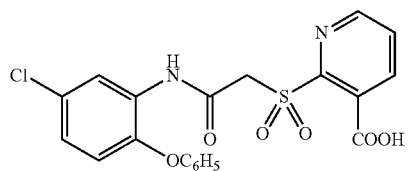

2c
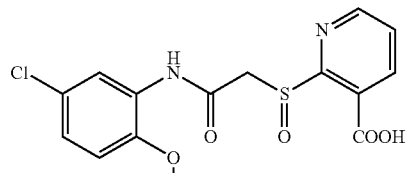

6a
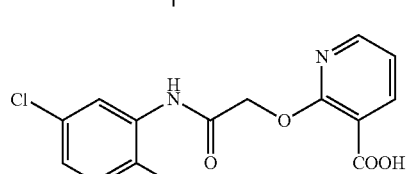

6b
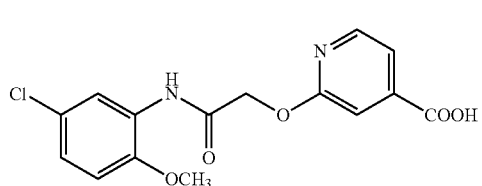

A second aspect of the present disclosure is to provide a method for producing the above nicotinic acid- or isonicotinic acid-based compound, and a pharmaceutically acceptable salt, ester, solvate thereof, comprising method A or method B as below:

said method A comprises the steps of: subjecting the compound as shown in Formula II to an oxidation reaction, and completing the reaction to obtain the compound as shown in Formula I;

Formula II
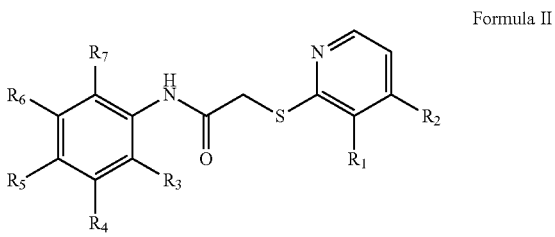

wherein $R_1$, $R_2$, $R_3$, $R_4$, $R_5$, $R_6$, and $R_7$ in the Formula II are defined as that in the Formula I;

said method B comprises the steps of:

1) reacting a compound as shown in Formula III with chloroacetyl chloride or bromoacetyl chloride to obtain a compound as shown in Formula IV;

Formula III
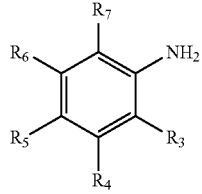

Formula IV
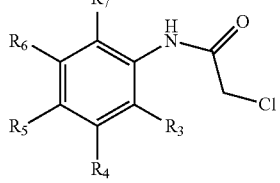

wherein $R_3$, $R_4$, $R_5$, $R_6$, and $R_7$ in the Formula III and Formula IV are defined as that in the Formula I;

2) subjecting the compound as shown in Formula IV to etherification with a compound as shown in Formula V to obtain the compound as shown in Formula I;

Formula V
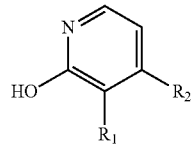

wherein $R_1$ and $R_2$ in the Formula V are defined as that in the Formula I.

In addition, use of the above compound as shown in Formula I provided by the present disclosure, or a pharmaceutically acceptable salt, ester, solvate thereof, or a mixture thereof, in the preparation of the following products, is also within the scope of protection of the present disclosure:

1) a medicament for preventing and/or treating *botulinum* toxin exposure and/or poisoning;
2) an inhibitor of *botulinum* toxin endopeptidase.

The present disclosure also provides an inhibitor of *botulinum* toxin endopeptidase, the active ingredient of which is the above compound as shown in Formula I provided by the present disclosure, or a pharmaceutically acceptable salt, ester, solvate thereof, or a mixture thereof.

The present disclosure also provides a medicament for preventing and/or treating *botulinum* toxin exposure and/or poisoning, the active ingredient of which is the above compound as shown in Formula I provided by the present disclosure, or a pharmaceutically acceptable salt, ester, solvate thereof, or a mixture thereof.

The present disclosure also provides a pharmaceutical preparation for preventing and/or treating *botulinum* toxin exposure and/or poisoning, the active ingredient of which is the above compound as shown in Formula I provided by the present disclosure, or a pharmaceutically acceptable salt, ester, solvate thereof, or a mixture thereof.

The present disclosure also provides use of a specific substance for inhibiting *botulinum* toxin endopeptidase; the active ingredient of the specific substance is the above compound as shown in Formula I provided by the present disclosure, or a pharmaceutically acceptable salt, ester, solvate thereof, or a mixture thereof.

Said specific substance is a medicament or a pharmaceutical preparation.

The present disclosure also provides use of a specific substance for preventing and/or treating *botulinum* toxin exposure and/or poisoning; the active ingredient of the specific substance is the above compound as shown in Formula I provided by the present disclosure, or a pharmaceutically acceptable salt, ester, solvate thereof, or a mixture thereof.

Said specific substance is a medicament or a pharmaceutical preparation.

As for the use, or the inhibitor of the *botulinum* toxin endopeptidase, or the medicament, or the pharmaceutical preparation above, said *botulinum* toxin may specifically comprise *botulinum* toxin type A and *botulinum* toxin type B.

The medicament above may be introduced into the body, such as muscle, intradermal, subcutaneous, vein, mucosal tissues by means of injection, spraying, nasal dropping, eye dropping, infiltration, absorption, physical or chemical mediation; or may be introduced into the body after being mixed with or encapsulated by other substances.

One or more pharmaceutically acceptable carriers may also be added to the above medicament when necessary. Said carriers comprise conventional diluents, excipients, fillers, binders, wetting agents, disintegrating agents, absorption enhancers, surfactants, adsorption carriers, lubricants and the like in the pharmaceutical field.

Said medicament may be formulated into various forms such as an injection, a suspension, a powder, a tablet, a granule, and the like. The various dosage forms of the medicament above may be prepared according to a conventional method in the pharmaceutical field.

DETAILED DESCRIPTION

Hereinafter, the present disclosure is further illustrated in conjunction with the specific examples, but the present disclosure is not limited to the examples. The methods mentioned are conventional methods unless otherwise specified. The raw materials mentioned can be commercially available unless otherwise specified.

EXAMPLE 1

Synthesis of 2-((2-((5-chloro-2-methoxyphenyl) amino)-2-oxoethyl)sulfonyl)isonicotinic acid 30 mg of 2-((2-((5-chloro-2-methoxyphenyl)amino)-2-oxoethyl)thio)isonicotinic acid was weighed and dissolved in 3 mL of anhydrous acetic acid, and 0.2 mL of hydrogen peroxide was slowly added thereto. The reaction was carried out at room temperature for 2 h, and a white solid was obtained by column purification with a yield of 42%.

Structural confirmation results of the product were as follows:

$^1$H NMR (300 MHz, DMSO-$d_6$) δ: 9.86 (s, 1H), 8.97 (d, J=4.9 MHz, 1H), 8.29 (s, 1H), 8.15 (dd, J=1.2, 4.9 MHz, 1H), 7.92 (d, J=2.4 MHz, 1H), 7.04-7.16 (m, 2H), 4.92 (s, 2H), 3.84 (s, 3H); ESI-MS (m/z): 383.06 (M–H$^+$), 766.87 (2M–H$^+$). As can be seen from the above, the compound had the correct structure, and the compound of interest was numbered as 2a.

2a

EXAMPLE 2

Synthesis of 2-((2-((5-chloro-2-phenoxyphenyl) amino)-2-oxoethyl)sulfonyl)nicotinic acid The same procedures as above were followed, except that 2-((2-((5-chloro-2-methoxyphenyl)amino)-2-oxoethyl)thio) isonicotinic acid was replaced with 2-((2-((5-chloro-2-phenoxyphenyl)amino)-2-oxoethyl)thio)nicotinic acid, to obtain 2-((2-((5-chloro-2-phenoxyphenyl)amino)-2-oxoethyl)sulfonyl)nicotinic acid. The product was a white solid with a yield of 53%.

Structural confirmation results of the product were as follows:

$^1$H NMR (300 MHz, DMSO-$d_6$) δ: 10.03 (s, 1H), 8.42 (d, J=7.4 MHz, 1H), 8.21 (s, 1H), 7.99 (s, 1H), 7.51 (d, J=7.5 MHz, 2H), 7.32-7.44 (m, 3H), 7.11 (s, 2H), 6.75 (t, 1H), 5.29 (s, 2H), 5.13 (s, 2H); ESI-MS (m/z): 459.01 (M–H$^+$). As can be seen from the above, the compound had the correct structure, and the compound of interest was numbered as 2b.

2b

EXAMPLE 3

Synthesis of 2-((2-((5-chloro-2-methoxyphenyl) amino)-2-oxoethyl)sulfinyl)nicotinic acid The same procedures as above were followed, except that 2-((2-((5-chloro-2-methoxyphenyl)amino)-2-oxoethyl)thio) isonicotinic acid was replaced with 2-((2-((5-chloro-2-methoxyphenyl)amino)-2-oxoethyl)thio)nicotinic acid, to obtain 2-((2-((5-chloro-2-methoxyphenyl)amino)-2-oxoethyl)sulfinyl)nicotinic acid. The product was a white solid with a yield of 48%.

Structural confirmation results of the product were as follows:

$^1$H NMR (300 MHz, DMSO-d$_6$) δ: 7.97 (s, 1H), 8.68 (dd, J=1.6, 4.8 MHz, 1H), 8.28 (dd, J=1.6, 7.7 MHz, 1H), 8.18 (d, J=2.2 MHz, 1H), 7.35 (q, 1H), 6.98-7.09 (m, 2H), 4.00 (s, 2H), 3.78 (s, 3H); ESI-MS (m/z): 383.17 (M–H$^+$), 767.01 (2M–H$^+$). As can be seen from the above, the compound had the correct structure, and the compound of interest was numbered as 2c.

2c

EXAMPLE 4

Synthesis of 2-(2-((5-chloro-2-methoxyphenyl) amino)-2-oxoethoxy)nicotinic acid 0.5 g of 2-methoxy-5-chloroaniline was weighed and dissolved in 10 mL of anhydrous dichloromethane, to which 1 mL triethylamine was added, and the mixture was placed in a 50 mL eggplant bottle. 0.25 mL of chloroacetyl chloride was accurately weighed and diluted in 2 mL of anhydrous dichloromethane. The mixture was slowly added dropwise to the reaction flask, and the reaction was carried out at room temperature for 4 h. The reaction was quenched with water, and the product was extracted with dichloromethane 3 times. The organic phases were combined and concentrated, and purified by column chromatography, to obtain 2-chloro-N-(5-chloro-2-methoxyphenyl)acetamide with a yield of 78%.

$^1$H NMR (300 MHz, DMSO-d$_6$) δ: 9.68 (s, 1H), 8.12 (d, J=2.5 MHz, 1H), 7.19 (dd, J=2.6, 8.8 MHz, 1H), 7.12 (d, J=8.8 MHz, 1H), 4.43 (s, 2H), 3.89 (s, 3H); ESI-MS (m/z): 272 (M+K$^+$).

0.1 g of 2-chloro-N-(5-chloro-2-methoxyphenyl) acetylamine, 0.56 g of 2-hydroxynicotinic acid, 0.19 g of potassium carbonate were weighed and placed in a 20 mL eggplant bottle, to which 5 mL of N, N-dimethylformamide was added, and the etherification was carried out overnight at room temperature. The product was extracted with a large amount of water and ethyl acetate. The organic phases were combined and concentrated, and purified by column chromatography, to obtain 2-(2-((5-chloro-2-methoxyphenyl) amino)-2-oxoethoxy)nicotinic acid as a white solid with a yield of 57%.

Structural confirmation results of the product were as follows:

$^1$H NMR (300 MHz, DMSO-d$_6$) δ: 10.02 (s, 1H), 8.42 (d, J=7.2 MHz, 1H), 8.22 (d, J=6.7 MHz, 1H), 8.04 (s, 1H), 7.10 (m, 2H), 6.75 (t, 1H), 5.11 (s, 2H), 3.87 (s, 3 H); ESI-MS (m/z): 335.31 (M–H$^+$). As can be seen from the above, the compound had the correct structure, and the compound of interest was numbered as 6a.

6a

EXAMPLE 5

Synthesis of 2-(2-((5-chloro-2-methoxyphenyl) amino)-2-oxoethoxy)isonicotinic acid The same procedures as above were followed, except that 2-hydroxynicotinic acid was replaced with 2-hydroxyisonicotinic acid, to obtain a white solid with a yield of 62%.

Structural confirmation results of the product were as follows:

$^1$H NMR (300 MHz, DMSO-d$_6$) δ: 9.82 (s, 1H), 8.08 (d, J=2.0 MHz, 1H), 7.63 (d, J=6.8 MHz, 1H), 7.33 (d, J=6.7 MHz, 1H), 7.09-7.12 (m, 1H), 6.80 (d, J=9.8 MHz, 1H), 6.54 (dd, J=1.5, 6.8 MHz, 1H), 4.85 (s, 2H), 3.87 (s, 3H); ESI-MS (m/z): 335.15 (M–H$^+$). As can be seen from the above, the compound had the correct structure, and the compound of interest was numbered as 6b.

6b

EXAMPLE 6

Inhibitory Effects of Novel Thionicotinic Acid-Based Compounds on Endopeptidase Activity of *Botulinum* Toxin Type A In Vitro The activities of the compounds were detected by substrate cleavage method. Reference was made to the literature (L. Li, B. R. Singh, High-Level expression, purification, and characterization of recombinant type A *botulinum* neurotoxin light chain, *Protein Expr Purif.* 1999, 17: 339-344) for expression and purification of *Botulinum* toxin type A endopeptidase (BoNT/A-LC). Reference was made to the literature (D. R. Ruge, F. M. Dunning, T. M. Piazza, B. E. Molles, M. Adler, F. N. Zeytin, W. C. Tucker, Detection of six serotypes of *botulinum* neurotoxin using fluorogenic reporters, *J. Anal. Biochem.* 2011, 411:200-209) for construction, expression and purification of CYA, a substrate of *Botulinum* toxin type A. To 50 µl of reaction solution (50 mM Hepes-NaOH pH 7.4, 10 mM NaCl, 0.1% Tween 20, 5 mM dithiothreitol, 10 μM $ZnCl_2$), BoNT/A-LC with a final concentration of 10 nM, and 100 μg of the compounds were added, which were incubated together for 15 min at 37° C., and then the substrate CYA (for *Botulinum* toxin type A) with a final concentration of 4 μM was added thereto, and the cleavage was carried out in vitro for 30 min SDS-PAGE detection and analysis were performed by a gel imaging system (Bio-Rad Company, Molecular Imager chemiDoc™ XRS Imaging System), and gel image capture was performed by a gel acquisition and image analysis system (ChampGel 5000 Plus Company, SAGECREATION). The data was analyzed and processed by a software Gel-Pro analyzer, and protein fragment gray scale analysis was performed. The inhibition rates of the compounds were calculated in comparison with the control group.

Results of the inhibitory activities of the compounds in vitro detected by substrate cleavage method were shown in Table 1. The compounds had different inhibitory effects on the endopeptidase activity of *Botulinum* toxin type A, with an inhibition rate in the range from 0 to 60.0%. Among them, the compound as shown in 2c obtained in Example 1 had a remarkable inhibitory effect and the inhibition rate could reach 60.0%.

TABLE 1

Inhibitory effects of compounds on Botulinum toxin type A detected by substrate cleavage method

| | Compounds dissolved in aqueous 20% by volume of 1,3-propanediol solution No. | | | | |
|---|---|---|---|---|---|
| | 2a | 2b | 2c | 6a | 6b |
| Inhibition rate % | 10 | 5 | 60 | 0 | 0 |

EXAMPLE 7

Inhibitory Effects of Novel Thionicotinic Acid-Based Compounds on Endopeptidase Activity of *Botulinum* Toxin Type B In Vitro The activities of the compounds were detected by substrate cleavage method. Reference was made to the literature (J. Gilsdorf, N. Gul, L. A. Smith, Expression, purification, and characterization of *Clostridium botulinum* type B light chain, *Protein Expr Purif* 46 (2006) 256-267) for expression and purification of *Botulinum* toxin type B endopeptidase (BoNT/B-LC). Reference was made to the literature (D. R. Ruge, F. M. Dunning, T. M. Piazza, B. E. Molles, M. Adler, F. N. Zeytin, W. C. Tucker, Detection of six serotypes of *botulinum* neurotoxin using fluorogenic reporters, *J. Anal. Biochem.* 2011, 411:200-209) for construction, expression and purification of CYB, a substrate of *Botulinum* toxin type B. To 50 μl of reaction solution (50 mM Hepes-NaOH pH 7.4, 10 mM NaCl, 0.1% Tween 20, 5 mM dithiothreitol, 10 μM $ZnCl_2$), BoNT/B-LC with a final concentration of 10 nM, and 100 μg of the compounds were added, which were incubated together for 15 min at 37° C., and then the substrate CYB (for *Botulinum* toxin type B) with a final concentration of 4 μM was added thereto, and the cleavage was carried out in vitro for 30 min SDS-PAGE detection and analysis were performed by a gel imaging system (Bio-Rad Company, Molecular Imager chemiDoc™ XRS Imaging System), and gel image capture was performed by a gel acquisition and image analysis system (ChampGel 5000 Plus Company, SAGECREATION). The data was analyzed and processed by a software Gel-Pro analyzer, and protein fragment gray scale analysis was performed. The inhibition rates of the compounds were calculated in comparison with the control group.

Results of the inhibitory activities of the compounds in vitro detected by substrate cleavage method were shown in Table 1. The compounds had different inhibitory effects on the endopeptidase activity of *Botulinum* toxin type B, with an inhibition rate in the range from 0 to 85.0%. Among them, the compound as shown in 6b obtained in Example 2 had a remarkable inhibitory effect and the inhibition rate could reach 85.0%, followed by the compound as shown in 6a obtained in Example 2 which had an inhibition rate of 80%.

TABLE 2

Inhibitory effects of compounds on Botulinum toxin type B detected by substrate cleavage method

| | Compounds dissolved in aqueous 20% by volume of 1,3-propanediol solution No. | | | | |
|---|---|---|---|---|---|
| | 2a | 2b | 2c | 6a | 6b |
| Inhibition rate % | 0 | 0 | 35 | 80 | 85 |

EXAMPLE 8

Protection Effects of Novel Thionicotinic Acid-Based Compounds against *Botulinum* Toxin Type A Poisoning in Animals Reference was made to the literature (C. J. Malizio, M. C. Goodnough, E. A. Johnson, Purification of *Clostridium botulinum* type A neurotoxin, *Methods Mol Biol.* 2000, 145:27-39) for extraction and identification of *Botulinum* toxin type A (BoNT/A), and Balb/c mice of 16-18 g were purchased from the Laboratory Animal Center of the Academy of Military Medical Sciences. Reference was made to the method for mouse botulism model described in the literature (C. H. Hatheway, J. D. Snyder, J. E. Seals, T. A. Edell, G. E. Lewis, Jr. Antitoxin levels in botulism patients treated with trivalent equine botulism antitoxin to toxin types A, B, and E. *Infect Dis* 1984, 150: 145-151) for protection experiments against *botulinum* toxin poisoning. The method was briefly as follows: Balb/C mice were used as test animals, which were randomly divided into groups with 10 mice of each group, and 1 mg of various compounds were used as samples to be tested. The mice were given *Botulinum* toxin type A in an amount of 5-fold of the median lethal dose ($5LD_{50}$) by injection via the tail vein, and then the mice were given 1 mg of the compounds in a solution (dissolved in 20% of 1,3-propanediol) by injection via the tail vein. A blank group and a control group were set at the same time. The observation was continued for more than 5 days, to observe the symptoms of botulism in mice (such as the occurrence of wasp waist, horripilation, weak breathing, limb paralysis until death), record the survival time of mice, and calculate the survival rate.

The anti-toxic effects of the compounds in the mouse botulism model were shown in Table 36. The compounds could inhibit the lethal effect of *Botulinum* toxin type A in the test animals to different degrees. Among them, the compound as shown in 2c obtained in Example 1 showed the highest protection rate of 100%, followed by the compound as shown in 6a obtained in Example 2 which showed a protection rate of 60%.

TABLE 3

Anti-toxic effects of compounds in mouse model poisoned by Botulinum toxin type A

| Group | Antitoxin | Placebo | 2a | 2b | 2c | 6a | 6b |
|---|---|---|---|---|---|---|---|
| Survival rate % | 100 | 0 | 0 | 0 | 100 | 60 | 0 |

Note:
the placebo in Table 3 was a solvent (aqueous 20% by volume of 1,3-propanediol solution); the antitoxin was a type A horse serum antitoxin (purchased from National Institutes for Food and Drug Control).

EXAMPLE 9

Protection Effects of Thionicotinic Acid-Based Compounds against Botulinum Toxin Type B Poisoning in Animals Reference was made to the Literature (H. Arimitsu, K. Inoue, Y. Sakaguchi, J. Lee, Y. Fujinaga, T. Watanabe, T. Ohyama, R. Hirst, K. Oguma, Purification of fully activated *Clostridium botulinum* serotype B toxin for treatment of patients with dystonia, *Infect Immun.* 71(2003)1599-1603) for extraction and identification of *Botulinum* toxin type B (BoNT/B), and Balb/c mice of 14-16 g were purchased from the Laboratory Animal Center of the Academy of Military Medical Sciences.

Reference was made to the method for mouse botulism model described in the literature (C. H. Hatheway, J. D. Snyder, J. E. Seals, T. A. Edell, G. E. Lewis, Jr. Antitoxin levels in botulism patients treated with trivalent equine botulism antitoxin to toxin types A, B, and E. *Infect Dis* 1984, 150: 145-151) for protection experiments against *botulinum* toxin poisoning. The method was briefly as follows: Balb/C mice were used as test animals, which were randomly divided into groups with 10 mice of each group, and 1 mg of various compounds were used as samples to be tested. The mice were given *Botulinum* toxin type B in an amount of 3-fold of the median lethal dose ($3LD_{50}$) by injection via the tail vein, and then the mice were given 1 mg of the compounds in a solution (dissolved in 20% of 1,3-propanediol) by injection via the tail vein. A blank group and a control group were set at the same time. The observation was continued for more than 5 days, to observe the symptoms of botulism in mice (such as the occurrence of wasp waist, horripilation, weak breathing, limb paralysis until death), record the survival time of mice, and calculate the survival rate.

The anti-toxic effects of the compounds in the mouse botulism model were shown in Table 4. The compounds could inhibit the lethal effect of *Botulinum* toxin type B in the test animals to different degrees. Among them, the compound as shown in 6b obtained in Example 2 showed the highest protection rate of 80%, followed by the compound as shown in 2c obtained in Example 1 and the compound as shown in 6a obtained in Example 2, both of which showed a protection rate of 20%.

TABLE 4

Anti-toxic effects of compounds in mouse model poisoned by Botulinum toxin type B

| Group | Antitoxin | Placebo | 2a | 2b | 2c | 6a | 6b |
|---|---|---|---|---|---|---|---|
| Survival rate % | 100 | 0 | 0 | 0 | 20 | 20 | 80 |

Note:
the placebo in Table 4 was a solvent (aqueous 20% by volume of 1,3-propanediol solution); the antitoxin was a type B horse serum antitoxin (purchased from National Institutes for Food and Drug Control).

INDUSTRIAL APPLICABILITY

The pharmacodynamic experiments have demonstrated that the thionicotinic acid-based compounds provided by the present disclosure can inhibit the endopeptidase activity of *botulinum* toxins in vitro, and also have evident protection effects in mice poisoned by *botulinum* toxins.

What is claimed is:
1. A compound of Formula I, or a pharmaceutically acceptable salt or solvate thereof,

Formula I in the Formula I,
$R_1$ and $R_2$ independently represent any one of the groups selecting from the group consisting of hydrogen and —$(CH_2)_m$COOH;
$R_3$, $R_4$, $R_5$, $R_6$ and $R_7$ independently represent any one of the groups selecting from the group consisting of hydrogen, hydroxyl, amino, halogen, lower alkyl, lower alkoxy, and lower cycloalkyl;
the lower alkyl refers to a linear or branched saturated aliphatic group having 1 to 6 carbon atoms;
the lower alkoxy refers to a linear or branched alkoxy group having 1 to 6 carbon atoms;
the lower cycloalkyl refers to a ring group having 3 to 7 carbon atoms;
X independently represents 0 or —S=O;
m is 0, or 1, or 2, or 3.
2. The compound of Formula I, or a pharmaceutically acceptable salt or solvate thereof according to claim 1, characterized in that the compound of Formula I is any one selected from the group consisting of:
2-((2-((5-chloro-2-methoxyphenyl)amino)-2-oxoethyl)sulfonyl)isonicotinic acid;
2-((2-((5-chloro-2-phenoxyphenyl)amino)-2-oxoethyl)sulfonyl)nicotinic acid;
2-((2-((5-chloro-2-methoxyphenyl)amino)-2-oxoethyl)sulfinyl)nicotinic acid;
2-(2-((5-chloro-2-methoxyphenyl)amino)-2-oxoethoxy)nicotinic acid;
2-(2-((5-chloro-2-methoxyphenyl)amino)-2-oxoethoxy)isonicotinic acid.

3. A pharmaceutical preparation comprising the compound of Formula I, or a pharmaceutically acceptable salt or solvate thereof according to claim 1, or a mixture thereof.

4. The pharmaceutical preparation according to claim 3, wherein the *botulinum* toxin comprises *botulinum* toxin type A and *botulinum* toxin type B.

* * * * *